United States Patent [19]

Jonsson et al.

[11] Patent Number: 4,957,745

[45] Date of Patent: Sep. 18, 1990

[54] PHARMACEUTICAL PREPARATION

[75] Inventors: Ulf E. Jonsson; John A. Sandberg, both of Mölndal; John A. Sjogren, Mölnycke, all of Sweden

[73] Assignee: Aktiebolaget Hassle, Molndal, Sweden

[21] Appl. No.: 310,489

[22] Filed: Feb. 14, 1989

Related U.S. Application Data

[63] Continuation of Ser. No. 907,510, Sep. 12, 1986, abandoned.

[30] Foreign Application Priority Data

Oct. 11, 1985 [SE] Sweden .................................. 8504721

[51] Int. Cl.$^5$ ............................ A61K 9/22; A61K 9/36
[52] U.S. Cl. ...................................... 424/461; 424/473; 424/480; 424/494; 424/475
[58] Field of Search ................ 424/458, 461, 462, 469, 424/470, 480, 489, 494, 495, 497, 561, 473

[56] References Cited

U.S. PATENT DOCUMENTS

| | | | |
|---|---|---|---|
| 3,726,897 | 4/1973 | Schindler et al. | 514/963 X |
| 3,951,821 | 4/1976 | Davidson | 252/1 |
| 4,083,949 | 4/1978 | Benedikt | 424/469 |
| 4,123,382 | 10/1978 | Morse et al. | 514/963 X |
| 4,169,069 | 9/1979 | Unger et al. | 514/963 X |
| 4,193,985 | 3/1980 | Bechgaard et al. | 424/462 |
| 4,256,108 | 3/1981 | Theeunes | 424/473 |
| 4,291,016 | 9/1981 | Nougaret | 424/494 |
| 4,309,404 | 1/1982 | Deneale et al. | 424/489 |
| 4,309,406 | 1/1982 | Guley et al. | 424/489 |
| 4,326,525 | 4/1982 | Swanson et al. | 424/473 |
| 4,341,759 | 7/1982 | Bogentoft et al. | 424/494 |
| 4,415,547 | 11/1983 | Yu et al. | 424/469 |
| 4,434,153 | 2/1984 | Urquhart et al. | 424/469 |
| 4,439,195 | 3/1984 | Swanson et al. | 424/473 |
| 4,449,983 | 5/1984 | Curtese et al. | 424/434 |
| 4,484,921 | 11/1984 | Swanson et al. | 424/473 |
| 4,510,150 | 4/1985 | Berthold | 514/338 |
| 4,578,075 | 3/1986 | Urquhart et la. | 424/458 |
| 4,587,267 | 5/1986 | Drake et al. | 514/769 |
| 4,642,233 | 2/1987 | Urquhart et al. | 424/486 |
| 4,649,043 | 3/1987 | Urquhart et al. | 424/486 |
| 4,681,583 | 7/1987 | Urquhart et al. | 423/467 |
| 4,681,755 | 7/1987 | Colombo et al. | 424/486 |
| 4,780,318 | 10/1988 | Appelgren et al. | 424/469 |

FOREIGN PATENT DOCUMENTS

| | | |
|---|---|---|
| 0013263 | 7/1980 | European Pat. Off. . |
| 0061217 | 9/1982 | European Pat. Off. . |
| 0123470 | 10/1984 | European Pat. Off. . |
| 0148811 | 7/1985 | European Pat. Off. . |
| 8503436 | 8/1985 | PCT Int'l Appl. . |
| 1542414 | 3/1979 | United Kingdom . |
| 2098867 | 12/1982 | United Kingdom . |
| 2159715 | 12/1985 | United Kingdom . |

OTHER PUBLICATIONS

Oros Drug Delivery Systems, Brit. J. Clin. Pharm., 19:695-765, 2135-2185, 2195-2245, (1985).

"Controlled Release From Dosage Forms", Bogentoft, C., and Sjogren, J., Dept. of Pharmaceutics, Hassle, Sweden, 1980 Elsevier/North-Holland Biomedical Press, Towards Better Saftey; Safety of Drugs and Pharmaceutical Products, pp. 229-246.

Primary Examiner—Shep K. Rose
Attorney, Agent, or Firm—White & Case

[57] ABSTRACT

Controlled release preparation containing a number of beads comprising a salt of metoprolo as the main soluble component, a method for the production thereof and the use in the treatment of cardiovascular disorders.

21 Claims, 3 Drawing Sheets

PHARMACEUTICAL PREPARATION

This application is a continuation of application Ser. No. 06/907,510, filed on 9/12/86 now abandoned.

FIELD OF THE INVENTION

The present invention is related to a new pharmaceutical preparation with controlled release of metoprolol, to a method for the manufacture of such a preparation and to a method for treatment of cardiovascular disorders using the new pharmaceutical preparation.

BACKGROUND OF THE INVENTION

Metoprolol, which has the structural formula

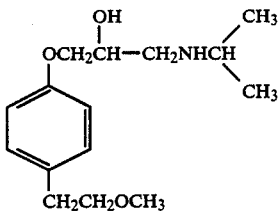

is known from e.g. DE-No. 2 106 209. The drug, which is a $\beta$-adrenoceptor antagonist has preferably been used as a salt, e.g. the tartrate.

Metoprolol blocks the adrenergic stimulation of the heart and thus reduces the oxygen demand of the cardiac tissue. Apparently, this explains its beneficial effects in angina pectoris and cardioprotective action in myocardial infarction. In addition metoprolol normalizes blood pressure in a large proportion of patients with arterial hypertension which probably is due to an additional action on the control of peripheral resistance to blood-flow.

For patients suffering from cardiovascular disorders it is advantageous to have a constant concentration of the administered drug in the blood. Thus, a controlled release of the drug over a long period of time is desirable. According to the most common treatment, the patients are ordered one fast dissolving tablet twice a day. This gives a varying concentration with high peak and trough values of the drug during the day.

For dosage once a day metoprolol has been incorporated in controlled release tablets of the insoluble matrix type, e.g. Durules ®. However the drug release from the matrix tablets is not satisfying as about 50 percent of the dose is released within a few hours after administration. It has thus been a demand to find a way to obtain a drug preparation having a more constant controlled release of the active component for approximately 20-24 hours, whereby smoother blood concentration and effect profiles will be obtained over the entire dosage interval.

A drug delivery system named Oros ® may be used to obtain a controlled release of e.g. metoprolol for once daily dosage. The system is described in U.S. Pat. No. 4,036,227 and in a supplement to British Journal of Clinical Pharmacology (1985), 19, 695-765 by Theeuwes F. et al. Oros ® is a single-unit system consisting of an osmotically active core composed mainly of the drug substance surrounded by a semipermeable membrane through which a single small opening is drilled. The release of the drug from the system remains constant as long as a steady osmotic pressure is maintained across the membrane. 50–60% of the total content of the drug is released at a constant rate.

In SE-A-8400085 it has been proposed to prepare an enteric coated product, containing e.g. metoprolol, and with slow release of the active compound close to the colon. Such a preparation does not give the constant and slow pH-independent release of metoprolol, which the preparation according to this invention gives.

Depot preparations comprising a large number of smaller units are also known e.g. from EP 13263. This patent describes pharmaceutically indifferent cores covered by the active compound. The cores are made of soluble material e.g. lactose.

There are advantages of a depot preparation comprising a large number of small units, each of which releases the drug at a controlled rate over a depot preparation consisting of one single unit, e.g. a matrix tablet or a tablet surrounded by a coating, which controls the release. It is for example possible to obtain a reproducible emptying of units from the stomach when the particles used are smaller than 1-2 mm. Cf. Bogentoft C. et al.: Influence of food on the absorption of acetylsalicylic acid from enteric-coated dosage forms. Europ J Clin Pharmacol 1978, 14, 351-355. Dispersion over a great area in the gastrointestinal canal gives a more reproducible total time of the passage which is of advantage for the absorption. Cf. Edgar B, Bogentoft C and Lagerström P O: Comparison of two enteric-coated acetylsalicylic acid preparations by monitoring steady-state levels of salicylic acid and its metabolites in plasma and urine. Biopharmaceutics & Drug Disposition 1984, 5, 251-260. In addition a multiple unit preparation is preferable to one single drug unit as the dose is spread out in the intestine. The risk of local irritation and accumulation of several doses due to constriction in the alimentary canal is also considerably lower.

A further advantage with a multiple unit preparation is that it may be divided into smaller portions all having the same absorption properties. This makes it possible to obtain greater flexibility in selecting the size of the dose.

OUTLINE OF THE INVENTION

The present invention is related to a preparation containing metoprolol as active ingredient and having a controlled rate of drug release during at least 15 hours. By making a preparation containing a large number of small compact particles all comprising a salt of metoprolol as the main soluble component and coated with a polymeric membrane containing derivatives of cellulose without protolysable groups it has been possible to prepare a suitable dosage form having a controlled rate of release of metoprolol, virtually independent of pH, during 16-24 hours.

The small particles, beads, containing metoprolol have a size of 0.25-2 mm, preferably 0.35-1.0 mm.

The beads may contain metoprolol alone or may consist of insoluble cores coated with metoprolol. The beads have a very high content of metoprolol, preferably 95-100 w/w % of the soluble part of the beads. The insoluble cores have a size of 0.1-1.0 mm, preferably 0.15–0.3 mm. Examples of insoluble cores according to the invention are silicon dioxide and small particles of glass.

The beads according to the invention are compact, which means that their porosity is less than 15 percent.

Figure 1:
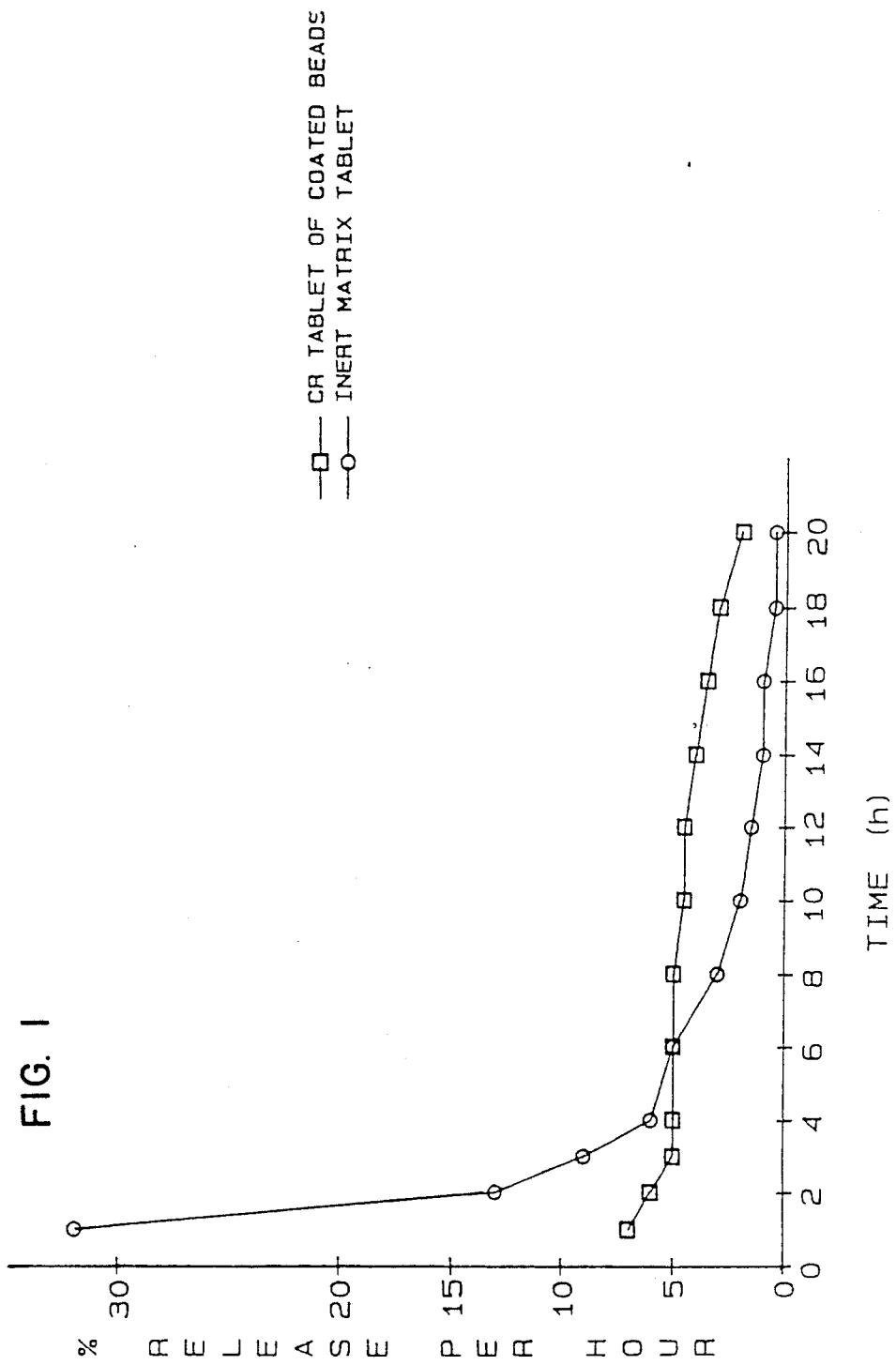
FIG. 1 shows the in vitro release of metoprolol.

As can be seen from FIG. 1 the new preparation is characterized in that at least 75% of the metoprolol is released within 20 hours and at least 50% of the dose of metoprolol is released at the rate 3–7 w/w %/hour.

Metoprolol used in the preparation may be in the form of the racemate, or one of the enantiomers, preferably the S-isomer.

Suitable soluble salts of metoprolol have a solubility less than 600 mg/ml in water at 25° C., preferably 30–600 mg/ml in water at 25° C. Examples of suitable salts are salts formed of organic carboxylic acids, preferably of low molecular weight. Especially preferred are the succinate, fumarate or bensoate of racemic metoprolol and the bensoate or sorbate of the S-enantiomer of metoprolol.

Very soluble salts, e.g. tartrate, hydrochloride are less suitable according to the present invention.

Examples of suitable polymeric materials are ethyl cellulose or a mixture of ethyl cellulose with hydroxypropylmethyl cellulose, hydroxypropyl cellulose, Eudragit RL or Eudragit RS.

Ethyl cellulose is available in variants having different grades of viscosity. According to the invention it is suitable to use ethyl cellulose having a viscosity between 10–50 cps, but also other types of ethyl cellulose may be used.

Eudragit ® is the trade name for a number of film-coating substances on an acrylic resin basis produced by Röhm Pharma. Eudragit RL and RS are copolymers synthetized from acrylic and methacrylic acid esters with a low content of quaternary ammonium groups. The molar ratio of these ammonium groups to the remaining neutral (meth)acrylic acid esters is 1:20 for Eudragit RL and 1:40 for Eudragit RS, resulting in different permeability characteristics.

Plasticizers and/or pigments may be added to the polymeric layer in order to improve the technical properties of the layer or change the permeability of the coating. Examples of suitable plasticizers are citrate esters, acetylated monoglycerides and glycerinetriacetate, especially preferred is acetyltributylcitrate.

The polymeric membrane is made of one or more polymers and gives a membrane with virtually pH-independent permeability characteristics within the pH range 1.0–8.0.

Each coated bead of metoprolol according to this invention forms an individual controlled release unit, releasing the drug at a predetermined rate. Therefore, the coated beads according to this invention make it possible to formulate and administer the preparation in different dosage forms. They can be filled into e.g. hard gelatin capsules or sachets or compressed to tablets and still give the desired plasma concentration profile and duration of the effect.

When the small coated particles of metoprolol are tabletted they are mixed with additives e.g. microcrystalline cellulose such as Avicel ®, which improves the tabletting properties and facilitates the disintegration of the tablet, whereby the individual beads are liberated.

The invention makes it possible to formulate pharmaceutical dosage forms which can be given once daily and still produce almost constant concentrations of the drug in the blood during the entire dosage interval until the next dose is administered.

Preparation

A process for the manufacture of the controlled release preparation represents a further aspect of the invention. After the initial forming of the beads containing metoprolol, the beads obtained are coated with the polymeric layer described in the examples. The polymeric mixture is dissolved in an organic solvent such as ethanol, isopropyl alcohol and/or methylene chloride. The spraying can be carried out in a coating pan, but is preferably carried out in a fluidized bed. Ethyl cellulose can also be applied from an aqueous dispersion (latex).

The preparation according to the invention is particularly advantageous in the treatment of cardiovascular disorders, and a method for the treatment of such conditions represents a further aspect of the invention.

The invention is described in detail in the following examples:

EXAMPLES

EXAMPLE 1

| | |
|---|---|
| Metoprolol fumarate | 1440 g |
| Methylene chloride | 9618 g |
| Ethanol 95% | 3888 g |
| SiO₂ (0.15–0.25 mm) | 375 g |
| Polymeric layer | |
| Ethyl cellulose 10 cps | 265.6 g |
| Hydroxypropylmethyl cellulose | 58.4 g |
| Acetyltributylcitrate | 36.0 g |
| Methylene chloride | 6141 g |
| Isopropylic alcohol | 1544 g |

In a fluidized bed granulator metoprolol fumarate was sprayed onto the cores of silicon dioxide from a solution of ethanol 95%. 400 g of the beads (granules) so formed (fraction 0.4–0.63 mm) were covered with the polymeric layer containing ethyl cellulose 10 cps, hydroxypropylmethyl cellulose and acetyltributylcitrate by spraying a solution of the mentioned substances in methylene chloride and isopropylic alcohol. The coated beads were then filled into hard gelatine capsules.

EXAMPLE 2

| | |
|---|---|
| Metoprolol succinate | 1440 g |
| Methylene chloride | 9618 g |
| Ethanol 95% | 3888 g |
| SiO₂ (0.15–0.25 mm) | 375 g |
| Polymeric layer | |
| Ethylcellulose 50 cps | 168.1 g |
| Hydroxypropylmethyl cellulose | 36.9 g |
| Acetyltributylcitrate | 22.8 g |
| Methylene chloride | 4167 g |
| Isopropylic alcohol | 815 g |
| Tablet additives | |
| Microcrystalline cellulose | 470.3 g |
| Maize starch | 117.6 g |
| Potato starch | 10.6 g |
| Water purified | 342.2 g |
| Magnesium stearate | 1.2 g |

Metoprolol succinate was sprayed onto the cores of silicon dioxide according to the process described in Example 1. 400 g of the granules so formed were coated with a polymeric film containing ethyl cellulose 50 cps, hydroxypropylmethyl cellulose and acetyltributylcitrate. An additional tablet mass was made by wet granulation of the dry mixture of microcrystalline cellulose and maize starch with the potato starchwater solution in a planetary mixer. Equal amounts (600 g) of the active and additional granules were finally mixed with Mg-stearate 0.1% and compressed to tablets.

EXAMPLE 3

Metoprolol succinate 100% in the form of compact spherical granules and having an average particle size of 0.42 mm.

400 g of the metoprolol succinate granules above with particles less than 0.63 mm were coated with

| Ethylcellulose 10 cps | 177.1 g |
|---|---|
| Hydroxypropylmethyl cellulose | 38.9 g |
| Acetyltributylcitrate | 24.0 g |
| Methylene chloride | 4094 g |
| Isopropylic alcohol | 1029 g |

The beads obtained were formed into pharmaceutical preparations as described above.

EXAMPLE 4

| Metoprolol succinate | 1440 g |
|---|---|
| Methylene chloride | 9618 g |
| Ethanol 95% | 3888 g |
| $SiO_2$ (0.15–0.25 mm) | 375 g |
| Polymeric layer | |
| Ethylcellulose N-10 | 166.2 g |
| Hydroxypropylmethyl cellulose | 39.0 g |
| Acetyltributylcitrate | 22.8 g |
| Methylene chloride | 3889 g |
| Isopropylic alcohol | 978 g |
| Tablet additives | |
| Microcrystalline cellulose | 429.3 g |
| Maize starch | 67.1 g |
| Lactose powder | 40.3 g |
| Polyvidone | 55.5 g |
| Water purified | 314.7 g |
| Magnesium stearate | 1.2 g |
| Tablet coating (12.500 tablets) | |
| Hydroxypropylmethyl cellulose | 159.6 g |
| Polyethylene glycol 6000 | 39.9 g |
| Colour Titanium Dioxide | 39.9 g |
| Water purified | 1356 g |
| Paraffin special | 1.6 g |

Metoprolol succinate was sprayed onto the cores of silicon dioxide according to the process described in Examples 1 and 2 above. 400 g of the so obtained beads (fraction 0.4–0.63 mm) were coated with the polymeric mixture also described above. The coated beads of metoprolol succinate obtained were mixed with the additives in equal portions and after addition of Mg-stearate 0.1%, the dry mixture was compressed to tablets. Finally, the tablets were coated in a coating pan with the tablet coating described above.

EXAMPLE 5

S-enantiomeric metoprolol sorbate in the form of compact spherical granules in the fraction 0.4–0.63 mm 40 g of the metoprolol sorbate granules above with particles less than 0.63 mm together with 360 g of nonpareil granules with particles between 0.75–1.0 mm were coated with

| Ethylcellulose 10 cps | 51.7 g |
|---|---|
| Hydroxypropylmethyl cellulose | 11.3 g |
| Acetyltributylcitrate | 7.0 g |
| Methylene chloride | 1194 g |
| Isopropylic alcohol | 300 g |

The beads obtained were formed into pharmaceutical preparations as described above.

Biopharmaceutical studies

Figure 2:
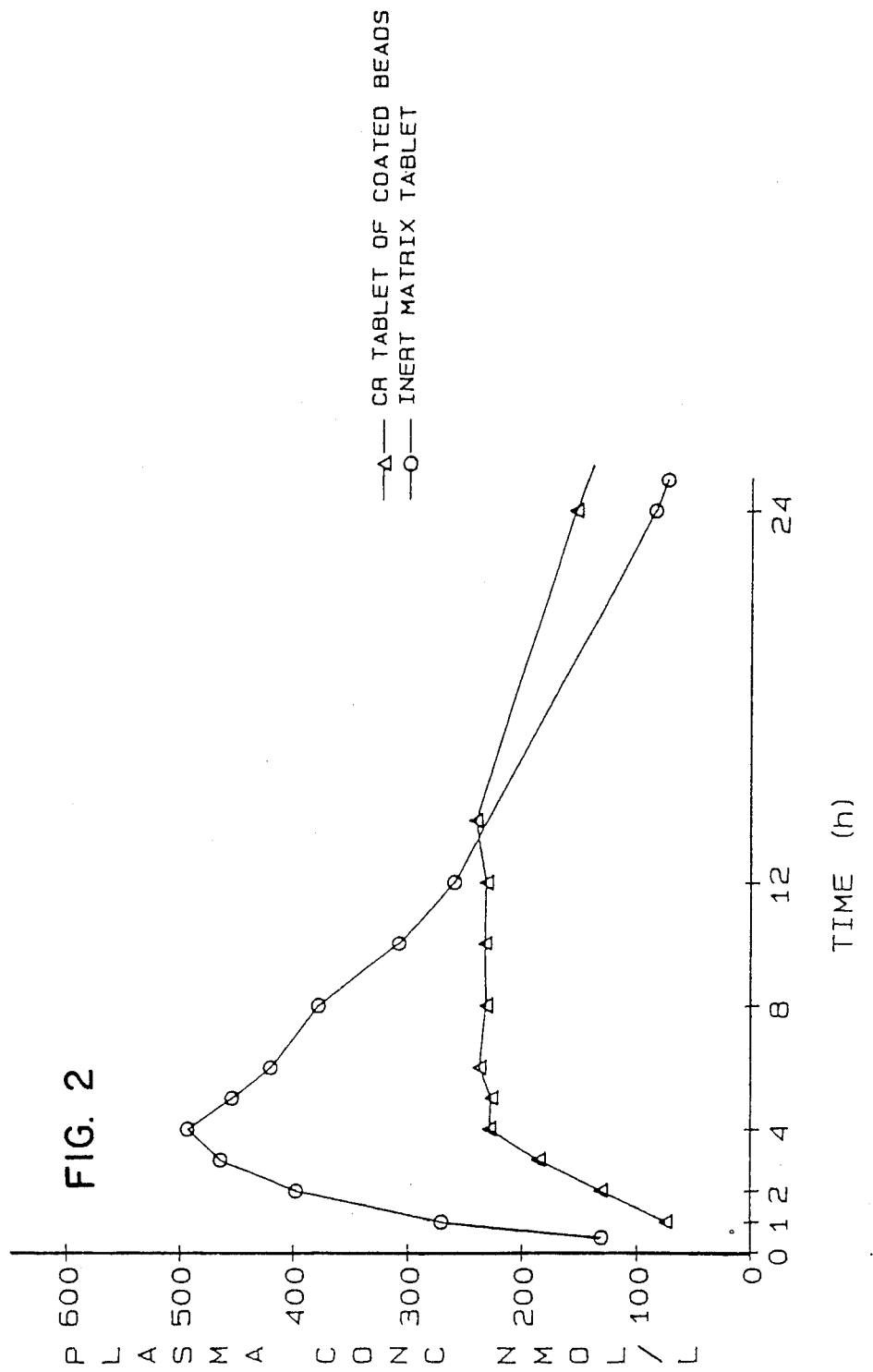
FIG. 2 shows the mean plasma concentration of metoprolol after single dose administration of the invention.

The plasma concentrations of metoprolol after a single dose of a controlled release preparation containing metoprolol succinate 190 mg according to example 4 of the description and the plasma concentrations after a single dose of Durules ® containing 200 mg of metoprolol tartrate are shown in the attached FIG. 2. 190 mg of the succinate salt is equivalent to 200 mg of metoprolol tartrate. The comparison has been carried out in 10 subjects. Each point represents the mean data from the 10 subjects. As can be seen the preparation according to the invention gives an almost constant concentration of metoprolol during more than 20 hours, whereas the insoluble matrix preparation gives unwanted high plasma concentration during the first hours after administration.

Figure 3:
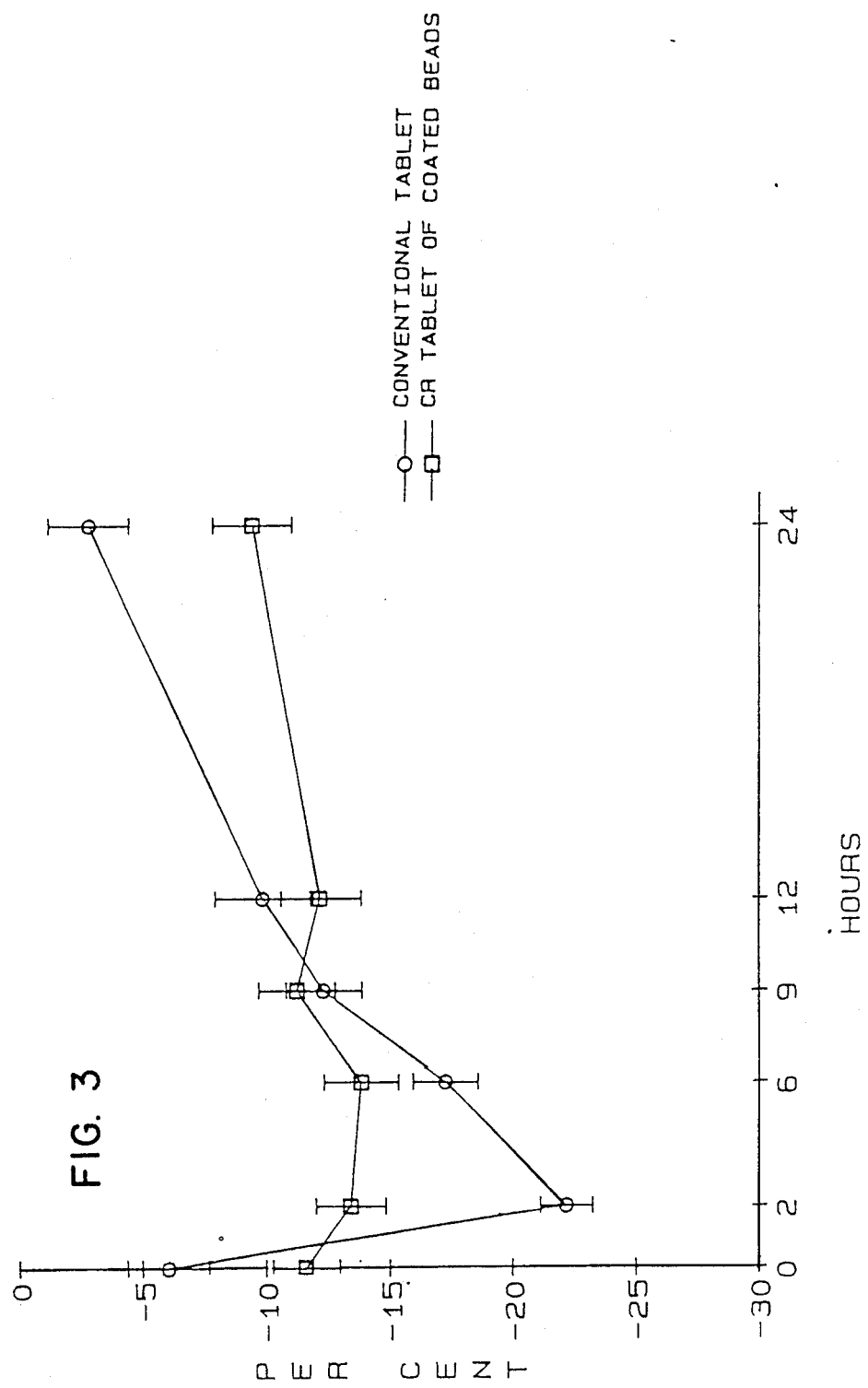
FIG. 3 shows the reduction of exercise heart rate on day 5 after daily administration of the invention.

Reduction of exercise heart rate 12 subjects were given an ordinary tablet containing 100 mg of metoprolol tartrate once a day and the reduction of the exercise heart rate on day 5 of the treatment was measured and compared with the reduction of the exercise heart rate on day 5 in subjects given a controlled release preparation according to Example 4 of the invention containing 95 mg metoprolol succinate (equivalent to 100 mg metoprolol tartrate). The reduction of the heart rate is illustrated in FIG. 3. As can be seen the preparation according to the invention gives an even pharmacodynamic effect for 24 hours.

The best mode of carrying out the invention is at present considered to be Example 4.

Table 1 illustrates the in vitro release of metoprolol from the compositions according to Examples 1-4. As can be seen from the table at least 50% of the dose of metoprolol is released at a rate varying between 3–7 w/w %/hour.

TABLE 1

Cumulative in vitro dissolution of metoprolol in a phosphate buffer pH 6.8.
Method: USP apparatus No. II, rotating paddle at 100 rpm.

| Example No. | Preparation | Percent released over time (h) | | | | | | | | | | | |
|---|---|---|---|---|---|---|---|---|---|---|---|---|---|
| | | 1 | 2 | 3 | 4 | 6 | 8 | 10 | 12 | 14 | 16 | 18 | 20 |
| 1 | capsule | 1 | 2 | 5 | 11 | 25 | 39 | 52 | 62 | 69 | 74 | 78 | 81 |
| 2 | tablet | 7 | 11 | 16 | 19 | 29 | 40 | 50 | 59 | 68 | 76 | 82 | 86 |
| 3 | capsule | 3 | 7 | 12 | 17 | 27 | 37 | 44 | 52 | 60 | 67 | 74 | 80 |
| 4 | tablet | 7 | 13 | 18 | 23 | 33 | 43 | 52 | 61 | 69 | 76 | 82 | 86 |
| 5 | capsule | 4 | 9 | 15 | 21 | 34 | 47 | 58 | 67 | 74 | 80 | 84 | 88 |

We claim:

1. Controlled release preparation comprising a plurality of beads having a soluble component comprising at least 95% weight/weight of a salt of metoprolol which has a solubility of less than 600 mg/ml in water at 25° C. and a metoprolol permeable polymeric membrane coating surrounding each of said beads, said coating consisting essentially of ethylcellulose or a mixture of ethylcellulose and hydroxypropylmethylcellulose wherein the coating is present in amounts such that the metoprolol is released through the coating over a period of at least 15 hours virtually independent of pH in the interval pH 1–8.

2. Preparation according to claim 1 wherein the size of the beads is in the range of 0.25–2 mm.

3. Preparation according to claim 2 wherein the size of the beads is in the range of 0.35–1.0 mm.

4. Preparation according to claim 1 wherein at least 50% of the dose of metoprolol is released at a rate of 3–7 w/w %/hour.

5. Preparation according to claim 1 wherein the salt of metoprolol has a solubility of 30–600 mg/ml.

6. Preparation according to claim 5 wherein the salt of metoprolol is formed of an organic carboxylic acid.

7. Preparation according to claim 6 wherein the salt of metoprolol is the succinate or fumarate of racemic metoprolol.

8. Preparation according to claim 6 wherein the salt of metoprolol is the bensoate or sorbate of the S-enantiomer of metoprolol.

9. Preparation according to claim 1 wherein the beads comprise at least 95 w/w % of metoprolol.

10. Preparation according to claim 1 wherein the beads further comprise an insoluble core disposed in the interior of the soluble component.

11. Preparation according to claim 10 wherein the insoluble cores have a size of 0.1–1.0 mm.

12. Preparation according to claim 10 wherein the insoluble cores have a size of 0.15–0.3 mm and are covered with a layer of the soluble component to give beads having a size of 0.35–1.0 mm.

13. Preparation according to claim 9 wherein the beads have a size of 0.35–1.0 mm.

14. Preparation according to claim 1 wherein polymeric membrane contains ethyl cellulose together with hydroxypropylmethyl cellulose.

15. A pharmaceutical preparation containing the controlled release preparation according to claim 1 filled into hard gelatine capsules.

16. A pharmaceutical preparation comprising the controlled release preparation according to claim 1 and pharmaceutical additives compressed to tablets which disintegrate to release the preparation when the tablets are brought into contact with gastro-intestinal fluids.

17. Method of producing a preparation according to claim 1 comprising spray coating beads comprising a salt of metoprolol with a membrane-forming solution consisting essentially of ethylcellulose.

18. A method for the treatment of cardiovascular disorders comprising administering a composition according to claim 1 to a host in need of such treatment in a therapeutically effective amount.

19. Preparation according to claim 10, wherein the insoluble cores have a size of 0.15–0.3 mm.

20. Preparation according to claim 1, wherein the amount of coating is such that at least 75% of the metoprolol is released over a period of 20 hours.

21. Preparation according to claim 1, wherein the soluble component comprises at least 95% w/w of the salt of metoprolol.

* * * * *